US006656221B2

(12) United States Patent
Taylor et al.

(10) Patent No.: US 6,656,221 B2
(45) Date of Patent: Dec. 2, 2003

(54) METHOD AND APPARATUS FOR IMPROVING MITRAL VALVE FUNCTION

(75) Inventors: Daniel C. Taylor, Brighton, MA (US); John R. Liddicoat, Sewickley, PA (US); Richard B. Streeter, Winchester, MA (US); Steven B. Woolfson, Boston, MA (US); William E. Cohn, Chestnut Hill, MA (US); Todd F. Davenport, Andover, MA (US); Thomas F. Kordis, Wilmington, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 10/068,264

(22) Filed: Feb. 5, 2002

(65) Prior Publication Data

US 2002/0183835 A1 Dec. 5, 2002

Related U.S. Application Data

(60) Provisional application No. 60/348,424, filed on Jan. 14, 2002, provisional application No. 60/339,481, filed on Oct. 26, 2001, provisional application No. 60/312,217, filed on Aug. 14, 2001, provisional application No. 60/283,820, filed on Apr. 13, 2001, provisional application No. 60/280,038, filed on Mar. 30, 2001, provisional application No. 60/279,973, filed on Mar. 29, 2001, provisional application No. 06/279,974, filed on Mar. 29, 2001, provisional application No. 60/278,153, filed on Mar. 23, 2001, provisional application No. 60/273,893, filed on Mar. 5, 2001, and provisional application No. 60/266,766, filed on Feb. 5, 2001.

(51) Int. Cl.$^7$ .................................................. A61F 2/24

(52) U.S. Cl. ..................................... 623/2.11; 623/2.36

(58) Field of Search ................................ 623/2.11, 2.36

(56) References Cited

U.S. PATENT DOCUMENTS

| 4,669,473 A | 6/1987 | Richards et al. |
| 4,917,698 A | 4/1990 | Carpentier et al. |

(List continued on next page.)

FOREIGN PATENT DOCUMENTS

| WO | 99/04730 | * | 2/1999 |
| WO | WO 01/00111 A1 | | 1/2001 |
| WO | WO 01/54618 A1 | | 8/2001 |
| WO | WO 02/053206 A2 | | 7/2002 |
| WO | WO 02/060352 A1 | | 8/2002 |
| WO | WO 02/062270 A1 | | 8/2002 |
| WO | WO 02/091908 A2 | | 11/2002 |
| WO | WO 02/100240 A2 | | 12/2002 |
| WO | WO 03/037171 A2 | | 5/2003 |

OTHER PUBLICATIONS

Buchanan, James W., Circumferential Suture of the Mitral Annulus for Correction of Mitral Regurgitation in Dogs, Veterinary Surgery, 1998, pp. 182–193.

Kerstetter, Kyle K. et al., Short–Term Hemodynamic Evaluation of Circumferential Mitral Annuloplasty for Correction of Mitral Valve Regurgitation in Dogs, Veterinary Surgery, 1998, pp. 216–223

Beardow, Andrew W. et al., Chronic Mitral Valve Disease in Cavalier King Charles Spaniels: 95 Cases (1987–1991), JAVMA, vol. 203, No. 7, Oct. 1, 1993, pp. 1023–1029.

Davila, Julio C. et al., Circumferential Suture of The Mitral Ring, 18 pages.

(List continued on next page.)

Primary Examiner—David H. Willse
Assistant Examiner—Thomas J Sweet
(74) Attorney, Agent, or Firm—Pandiscio & Pandiscio, P.C.

(57) ABSTRACT

A method and apparatus for reducing mitral regurgitation. The apparatus is inserted into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation and reduce mitral regurgitation.

47 Claims, 12 Drawing Sheets

U.S. PATENT DOCUMENTS

| | | | |
|---|---|---|---|
| 5,061,277 A | * 10/1991 | Carpentier et al. | ........ 623/2.36 |
| 5,092,889 A | 3/1992 | Campbell, Jr. | |
| 5,269,809 A | 12/1993 | Hayhurst et al. | |
| 5,332,402 A | 7/1994 | Teitelbaum | |
| 5,545,209 A | 8/1996 | Roberts et al. | |
| 5,720,726 A | 2/1998 | Marcadis et al. | |
| 5,800,495 A | 9/1998 | Machek et al. | |
| 5,800,526 A | 9/1998 | Anderson et al. | |
| 5,957,949 A | 9/1999 | Leonhardt et al. | |
| 5,980,570 A | 11/1999 | Simpson | |
| 6,051,020 A | 4/2000 | Goicoechea et al. | |
| 6,090,136 A | 7/2000 | McDonald et al. | |
| 6,162,245 A | 12/2000 | Jayaraman | |
| 6,187,040 B1 | 2/2001 | Wright | |
| 6,210,432 B1 | 4/2001 | Solem et al. | |
| 6,241,746 B1 | 6/2001 | Bosma et al. | |
| 6,332,896 B1 | 12/2001 | Hubbard et al. | |
| 6,402,781 B1 | 6/2002 | Langberg et al. | |
| 6,419,696 B1 | 7/2002 | Ortiz et al. | |
| 6,537,314 B2 | 3/2003 | Langberg et al. | |
| 6,569,198 B1 | 5/2003 | Wilson et al. | |
| 2001/0018611 A1 | 8/2001 | Solem et al. | |
| 2001/0044568 A1 | 11/2001 | Langberg et al. | |
| 2002/0016628 A1 | 2/2002 | Langberg et al. | |
| 2002/0087173 A1 | 7/2002 | Alferness et al. | |
| 2002/0103532 A1 | 8/2002 | Langberg et al. | |
| 2002/0103533 A1 | 8/2002 | Langberg et al. | |
| 2002/0151961 A1 | 10/2002 | Lashinski et al. | |
| 2002/0169502 A1 | 11/2002 | Mathis | |
| 2002/0169504 A1 | 11/2002 | Alferness et al. | |
| 2003/0069636 A1 | 4/2003 | Solem et al. | |
| 2003/0083538 A1 | 5/2003 | Adams et al. | |
| 2003/0093148 A1 | * 5/2003 | Bolling et al. | ............. 623/2.36 |
| 2003/0105520 A1 | 6/2003 | Alferness et al. | |

OTHER PUBLICATIONS

Glover, Robert P. et al., The Treatment of Mitral Valve Insufficiency By The Purse–String Technique, The Journal of Thoracic Surgery, Jan. 1957, 14 pages.

Davila, Julio C. et al., Circumferential Suture of The Mitral Valve for the Correction of Regurgitation, The American Journal of Cardiology, Inc., Sep. 1958, 6 pages.

Buchanan, James W., Causes and Prevalence of Cardiovascular Disease, Current Veterinary Therapy XI, WB Saunders Co., 1992, 2 pages.

* cited by examiner

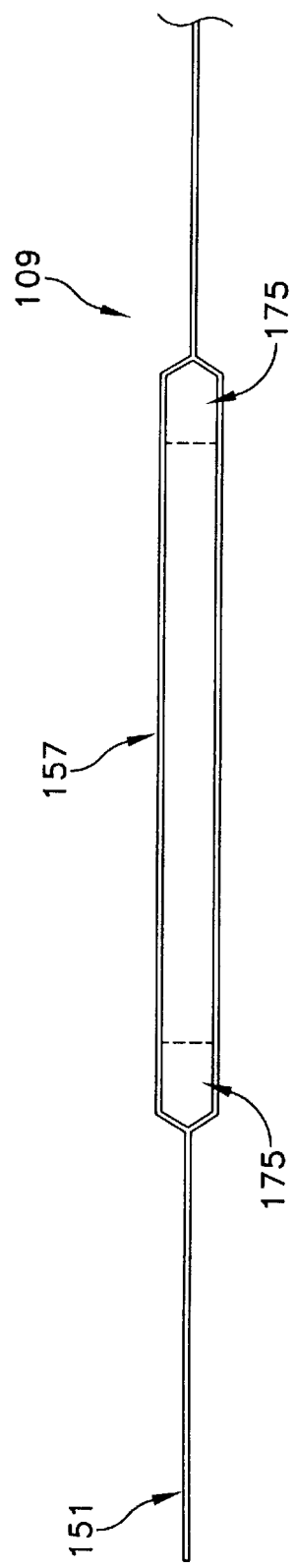
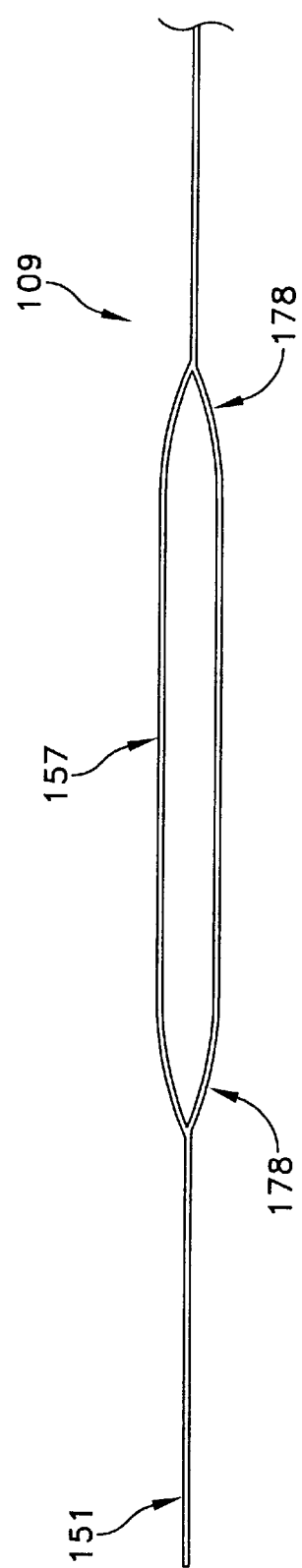
FIG. 10
FIG. 11

METHOD AND APPARATUS FOR IMPROVING MITRAL VALVE FUNCTION

REFERENCE TO PENDING PRIOR PATENT APPLICATIONS

This patent application claims benefit of:

(1) pending prior U.S. Provisional Patent Application Serial No. 60/266,766, filed Feb. 5, 2001 by William E. Cohn et al. for TRANSVASCULAR APPROACH TO MITRAL VALVE PROCEDURES;

(2) pending prior U.S. Provisional Patent Application Serial No. 60/273,893, filed Mar. 5, 2001 by William E. Cohn et al. for TRANSVASCULAR METHODS AND DEVICES FOR MITRAL VALVE PROCEDURES;

(3) pending prior U.S. Provisional Patent Application Serial No. 60/278,153, filed Mar. 23, 2001 by William E. Cohn et al. for METHOD AND APPPARATUS TO IMPROVE MITRAL VALVE FUNCTION;

(4) pending prior U.S. Provisional Patent Application Serial No. 60/279,974, filed Mar. 29, 2001 by Daniel C. Taylor et al. for METHOD AND APPARATUS TO IMPROVE MITRAL VALVE FUNCTION;

(5) pending prior U.S. Provisional Patent Application Serial No. 60/280,038, filed Mar. 30, 2001 by William E. Cohn et al. for METHODS AND APPARATUS FOR TEMPORARY IMPROVEMENT IN MITRAL VALVE FUNCTION;

(6) pending prior U.S. Provisional Patent Application Serial No. 60/279,973, filed Mar. 29, 2001 by Daniel C. Taylor et al. for METHODS AND DEVICES TO IMPROVE MITRAL VALVE FUNCTION;

(7) pending prior U.S. Provisional Patent Application Serial No. 60/283,820, filed Apr. 13, 2001 by William E. Cohn et al. for METHOD AND APPARATUS FOR TEMPORARY IMPROVEMENT IN MITRAL VALVE FUNCTION;

(8) pending prior U.S. Provisional Patent Application Serial No. 60/312,217, filed Aug. 14, 2001 by Daniel C. Taylor et al. for METHOD AND APPARATUS FOR TEMPORARY IMPROVEMENT IN MITRAL VALVE FUNCTION;

(9) pending prior U.S. Provisional Patent Application Serial No. 60/339,481, filed Oct. 26, 2001 by William E. Cohn et al. for TRANSVASCULAR APPROACH TO MITRAL VALVE PROCEDURES; and

(10) pending prior U.S. Provisional Patent Application Serial No. 60/348,424, filed Jan. 14, 2002 by Daniel C. Taylor et al. for METHOD AND APPARATUS TO IMPROVE MITRAL VALVE FUNCTION.

The aforementioned ten (10) patent applications are hereby incorporated herein by reference.

FIELD OF THE INVENTION

This invention relates to surgical methods and apparatus in general, and more particularly to surgical methods and apparatus for improving mitral valve function.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

In current practice, mitral valve surgery requires an extremely invasive approach that includes a chest wall incision, cardiopulmonary bypass, cardiac and pulmonary arrest, and an incision on the heart itself to gain access to the mitral valve. Such a procedure is associated with high morbidity and mortality. Due to the risk associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction.

Mitral regurgitation is a common occurrence in patients with heart failure and a source of important morbidity and mortality in these patients. Mitral regurgitation in patients with heart failure is caused by changes in the geometric configurations of the left ventricle, papillary muscles and mitral annulus. These geometric alterations result in incomplete coaptation of the mitral leaflets at systole. In this situation, mitral regurgitation is corrected by plicating the mitral valve annulus, either by sutures alone or by sutures in combination with a support ring, so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to cinch the annulus, in a pursestring-like fashion, to a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life and increases longetivity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for medical, interventional or surgical therapy.

SUMMARY OF THE INVENTION

As a result, one object of the present invention is to provide an improved method and apparatus for reducing mitral regurgitation.

Another object of the present invention is to provide a method and apparatus for reducing mitral regurgitation which is minimally invasive.

Another object of the present invention is to provide a method and apparatus for reducing mitral regurgitation which can be deployed either permanently (e.g., for patients suffering from heart failure) or temporarily (e.g., for patients suffering from mitral regurgitation with acute myocardial infarction).

These and other objects are addressed by the present invention, which comprises an improved method and apparatus for reducing mitral regurgitation.

In one form of the invention, there is provided a method for reducing mitral regurgitation comprising:

inserting apparatus into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to move at least a portion of the coronary sinus in the vicinity of the posterior leaflet of the mitral valve anteriorly, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to reduce the degree of natural curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to increase the natural radius of curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus having a distal end, a proximal end and an intermediate portion, the apparatus being configured so that when the apparatus is positioned in the coronary sinus in the vicinity of the posterior leaflet of the mitral valve, the distal and proximal ends will apply a posteriorly-directed force to the walls of the coronary sinus and the intermediate portion will apply an anteriorly-directed force to the walls of the coronary sinus, whereby to move the posterior annulus anteriorly and thereby improve leaflet coaptation.

In another form of the invention, there is provided a method for reducing mitral regurgitation comprising:

inserting a substantially straight elongated body into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation.

In another form of the invention, there is provided a method for reducing mitral regurgitation comprising:

inserting a substantially rigid elongated body into the coronary sinus of a patient in the vicinity of the posterior leaflet of the mitral valve, the substantially rigid elongated body being configured relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation.

In another form of the invention, there is provided a method for reducing mitral regurgitation comprising:

inserting a straight, substantially rigid elongated body into the coronary sinus of a patient in the vicinity of the posterior leaflet of the mitral valve, the length of the straight, substantially rigid elongated body being sized relative to the natural curvature of the coronary sinus in the vicinity of the posterior leaflet of the mitral valve so that when the straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation.

In another form of the invention, there is provided an apparatus for reducing mitral regurgitation comprising:

a body having a distal end, a proximal end and an intermediate portion, the body being configured so that when the body is positioned in the coronary sinus in the vicinity of the posterior leaflet of the mitral valve, the distal and proximal ends will apply a posteriorly-directed force to the walls of the coronary sinus, and the intermediate portion will apply an anteriorly-directed force to the walls of the coronary sinus, whereby to move the posterior annulus of the mitral valve anteriorly and thereby improve leaflet coaptation.

In another form of the invention, there is provided an apparatus for reducing mitral regurgitation comprising:

a substantially straight elongated body adapted to be inserted into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

In another form of the invention, there is provided an apparatus for reducing mitral regurgitation comprising:

a substantially rigid elongated body adapted to be inserted into the coronary sinus of a patient in the vicinity of the posterior leaflet of the mitral valve, the length of the straight, substantially rigid elongated body being sized relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation.

In another form of the invention, there is provided an apparatus for reducing mitral regurgitation comprising:

a straight, substantially rigid elongated body adapted to be inserted into the coronary sinus of a patient in the vicinity of the posterior leaflet of the mitral valve, the length of the straight, substantially rigid elongated body being sized relative to the natural curvature of the coronary sinus in the vicinity of the posterior leaflet of the mitral valve so that when the straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

Significantly, the present invention may be practiced in a minimally invasive manner, either permanently or temporarily, so as to reduce mitral regurgitation.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 10 and 11 show alternative constructions for the straight, substantially rigid elongated body;

DETAILED DESCRIPTION OF THE PREFERRED EMBODIMENTS

Figure 1:
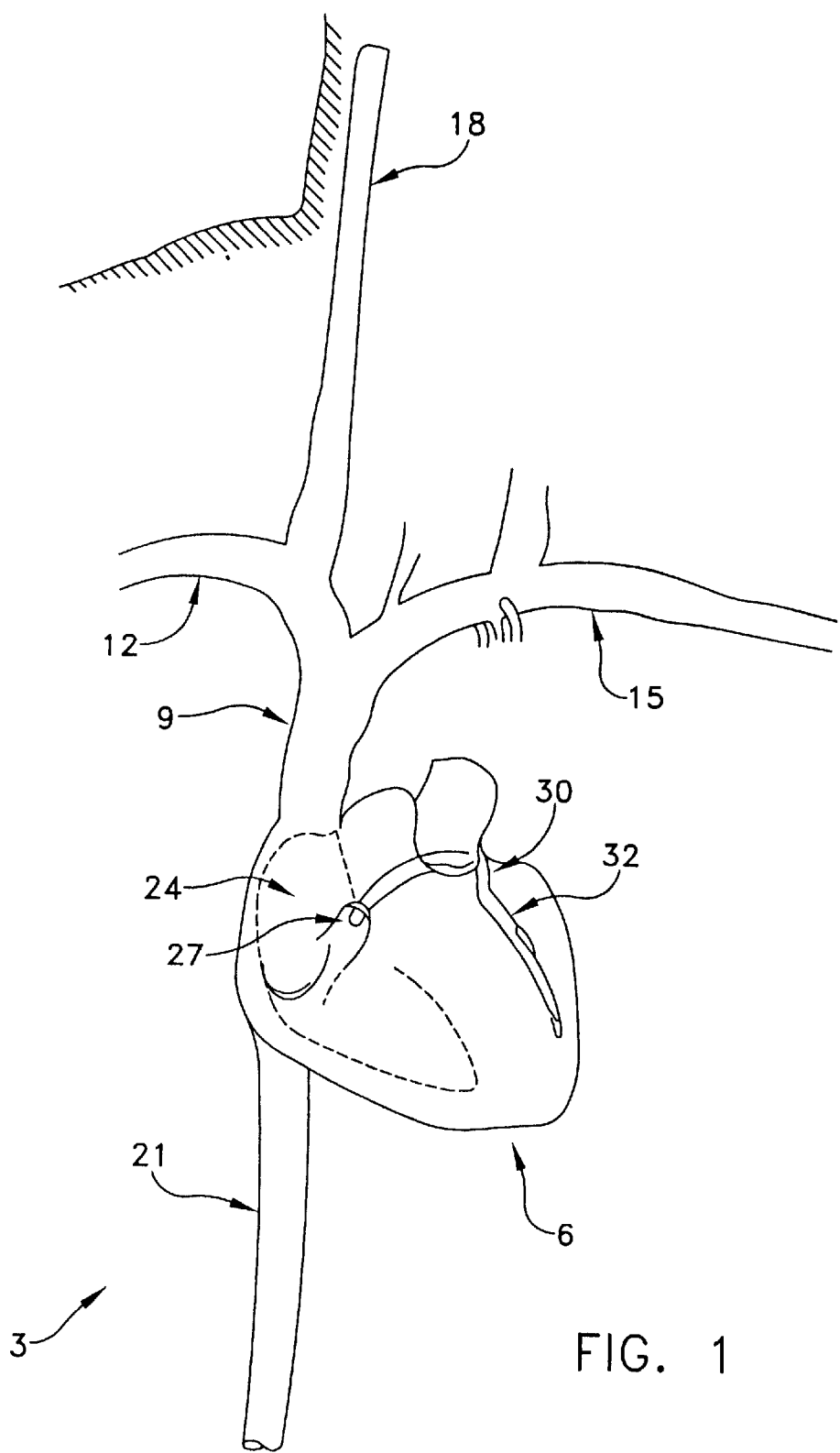
FIG. 1 is a schematic view of portions of the human vascular system.

The coronary sinus is the largest vein in the human heart. During a large portion of its course in the atrioventricular groove, the coronary sinus typically extends adjacent to the left atrium of the heart for a distance of approximately 5 to 10 centimeters. Significantly, for a portion of its length, e.g., typically approximately 7–9 cm, the coronary sinus extends substantially adjacent to the posterior perimeter of the mitral annulus. The present invention takes advantage of this fact. More particularly, by deploying novel apparatus in the coronary sinus, adjacent to the posterior leaflet of the mitral valve, the natural curvature of the coronary sinus may be modified in the vicinity of the posterior leaflet of the mitral valve, whereby to move the posterior annulus anteriorly so as to improve leaflet coaptation and, as a result, reduce mitral regurgitation.

In one preferred embodiment of the invention, the novel apparatus comprises a straight, substantially rigid elongated body, the length of the straight, substantially rigid elongated body being sized so that when the straight, substantially rigid body is positioned in the coronary sinus in the vicinity of the posterior leaflet of the mitral valve, the straight, substantially rigid elongated body will cause at least a portion of the coronary sinus to assume a substantially straight configuration adjacent to the posterior leaflet of the mitral valve, whereby to move the posterior annulus anteriorly and thereby improve leaflet coaptation.

And in one preferred embodiment of the invention, access to the coronary sinus is gained percutaneously, e.g., the straight, substantially rigid elongated body is introduced into the patient's vascular system via the jugular vein or via the left subclavian vein, passed down the superior vena cava, passed through the right atrium and then passed into the coronary sinus, where it is deployed. Alternatively, the straight, substantially rigid elongated body may be introduced into the coronary sinus through a small incision in the heart, or through some other incision into the patient's vascular system.

And in one preferred embodiment of the invention, the straight, substantially rigid elongated body is guided into position by (i) passing it through a pre-positioned catheter, or (ii) passing it over a pre-positioned guidewire, or (iii) passing it guide-free (e.g., on the end of a steerable delivery tool) to the surgical site.

Once deployed, the novel apparatus may be left in position permanently (e.g., in the case of patients suffering from mitral regurgitation associated with heart failure) or the novel apparatus may be left in position only temporarily (e.g., in the case of patients suffering from mitral regurgitation associated with acute myocardial infarction).

Visualization of the procedure may be obtained by fluoroscopy, echocardiography, intravascular ultrasound, angioscopy, real-time magnetic resonance imaging, etc. The efficacy of the procedure may be determined through echocardiography, although other imaging modalities may also be suitable.

Looking now at FIG. 1, there are shown aspects of the cardiovascular system 3 of a patient. More particularly, cardiovascular system 3 generally comprises the heart 6, the superior vena cava 9, the right subclavian vein 12, the left subclavian vein 15, the jugular vein 18, and the inferior vena cava 21. Superior vena cava 9 and inferior vena cava 21 communicate with the heart's right atrium 24. The coronary ostium 27 leads to coronary sinus 30. At the far end 31 (FIG. 2) of coronary sinus 30, the vascular structure turns into the vertically-descending anterior interventricular vein ("AIV") 32 (see FIG. 1). For purposes of the present invention, it can generally be convenient to consider the term "coronary sinus" to mean the vascular structure extending between coronary ostium 27 and AIV 32.

Figure 2:
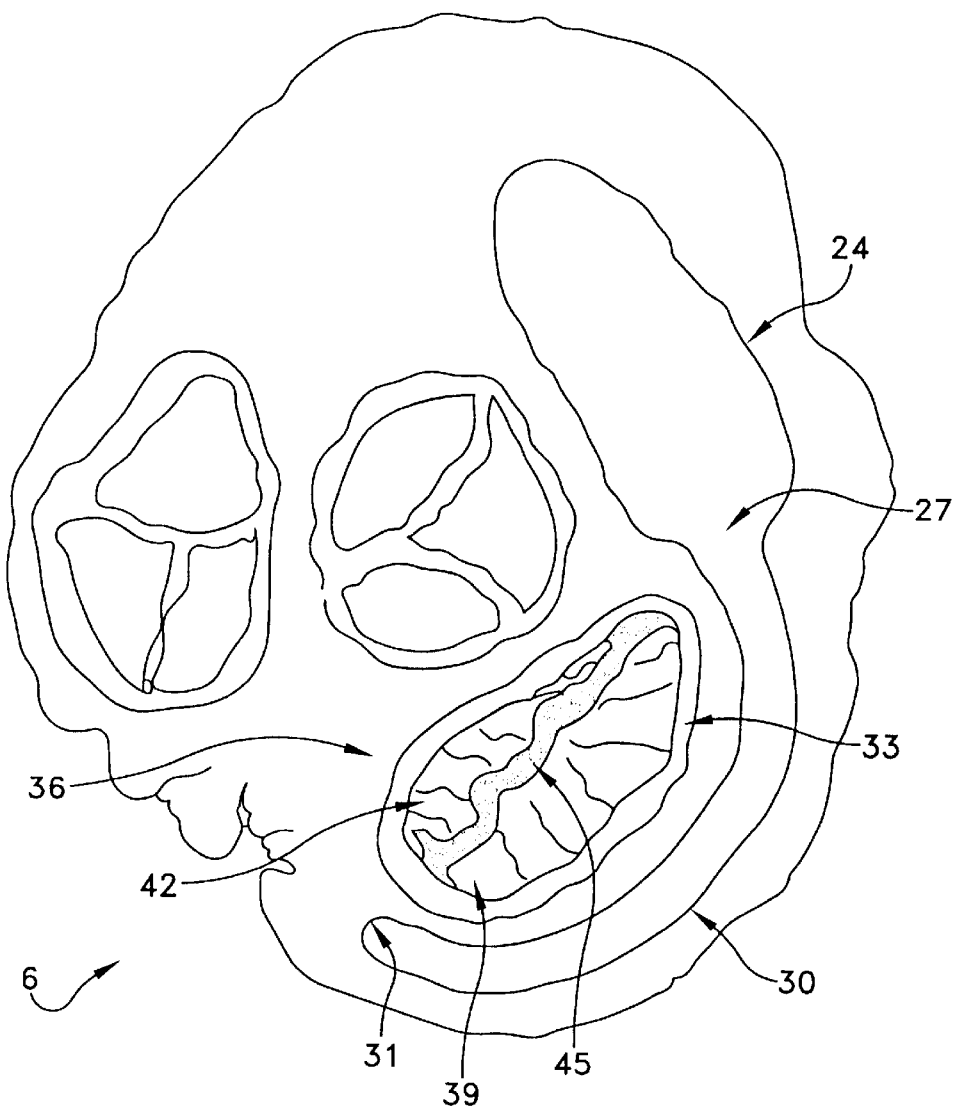
FIG. 2 is a schematic view of portions of the human heart.

As seen in FIG. 2, between coronary ostium 27 and AIV 32, coronary sinus 30 generally extends substantially adjacent to the posterior perimeter of the annulus 33 of the mitral valve 36. Mitral valve 36 comprises a posterior leaflet 39 and an anterior leaflet 42. In the case of a regurgitant mitral valve, posterior leaflet 39 and anterior leaflet 42 will generally fail to properly coapt at systole, thereby leaving an intervening gap 45 which will permit regurgitation.

Figure 3:
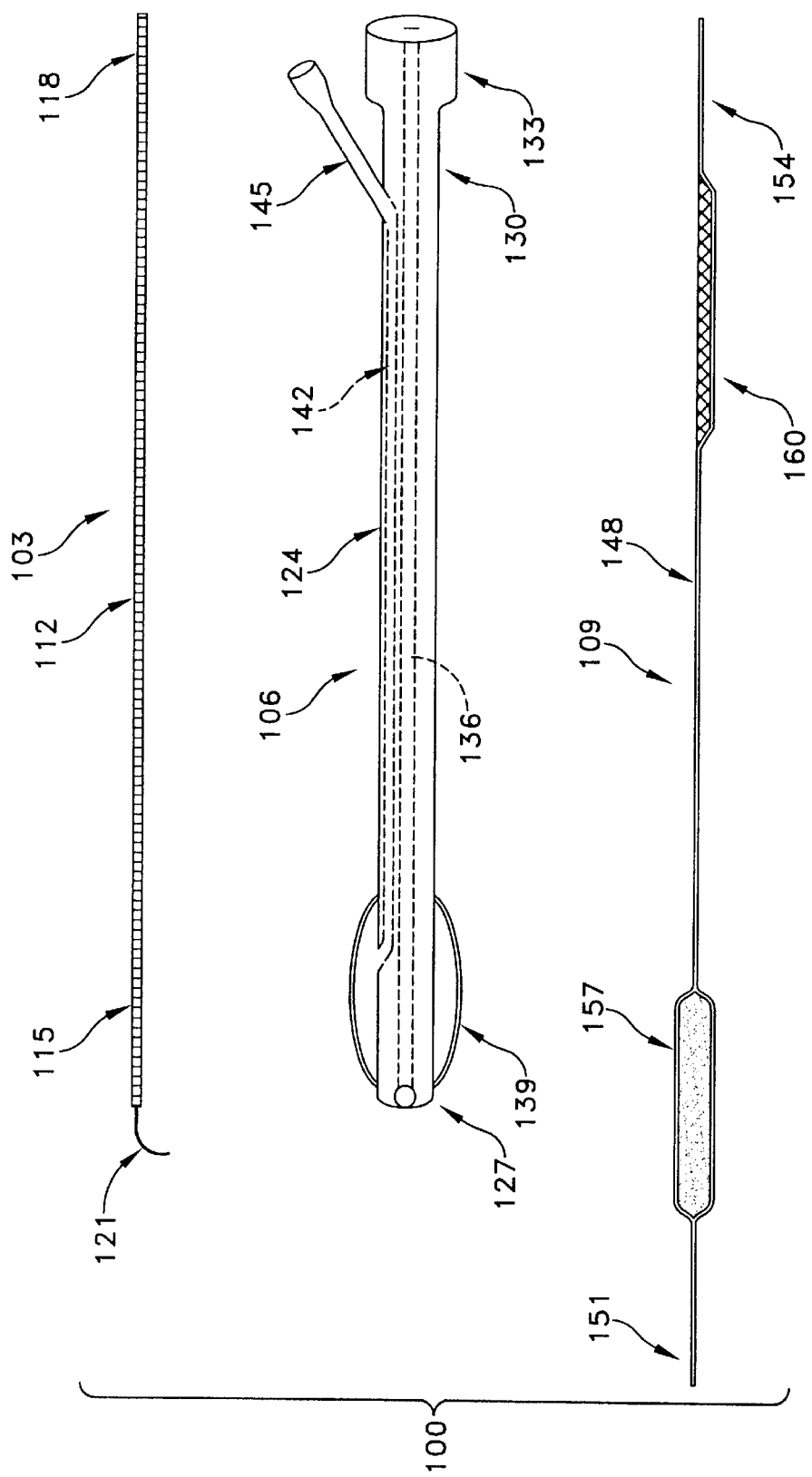
FIG. 3 is a schematic view of a preferred system formed in accordance with the present invention.

Looking next at FIG. 3, there is shown a system 100 which comprises one preferred embodiment of the present invention. More particularly, system 100 generally comprises a guidewire 103, a delivery catheter 106 and a push rod 109.

Guidewire 103 comprises a flexible body 112 having a distal end 115 and a proximal end 118. The distal end 115 of guidewire 103 preferably includes a spring tip 121 for allowing the distal end of guidewire 103 to atraumatically traverse vascular structures, i.e., while the guidewire is being passed through the vascular system of a patient.

Delivery catheter 106 comprises a flexible body 124 having a distal end 127 and a proximal end 130, preferably with an adjustable valve 133 attached. A central lumen 136 extends from distal end 127 to proximal end 130. In some circumstances it may be desirable to provide a, securing mechanism for securing the distal end of the delivery catheter within a vascular structure. By way of example but not limitation, a balloon 139 may be positioned about the exterior of flexible body 124, just proximal to distal end 127, with an inflation lumen 142 extending between balloon 139 and an inflation fitting 145.

Push rod 109 comprises a flexible body 148 having a distal end 151 and a proximal end 154. A straight, substantially rigid elongated body 157, which may have a variety of different lengths, is formed on flexible body 148, proximal to distal end 151. A removable proximal stiffener or handle 160 may be placed between straight, substantially rigid elongated body 157 and proximal end 154.

System 100 may be used as follows to reduce mitral regurgitation.

Figure 4:
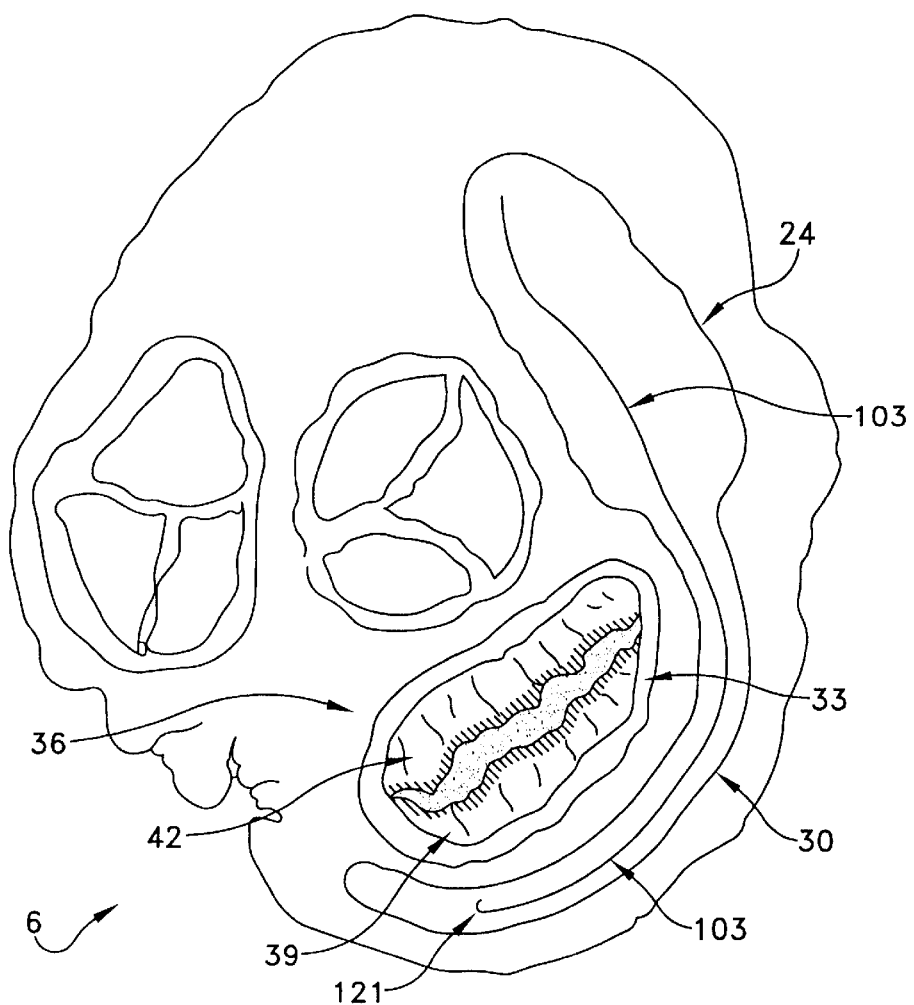
FIGS. 4–7 are a series of views illustrating use of the system of FIG. 3 to reduce mitral regurgitation.

First, distal end 115 of guidewire 103 is passed down the jugular vein 18 (or the left subclavian vein 15) of a patient, down superior vena cava 9, through right atrium 24 of the heart, and then into coronary sinus 30. See FIG. 4. It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 will help ensure minimal damage to vascular structures as guidewire 103 is maneuvered into position.

Figure 5:
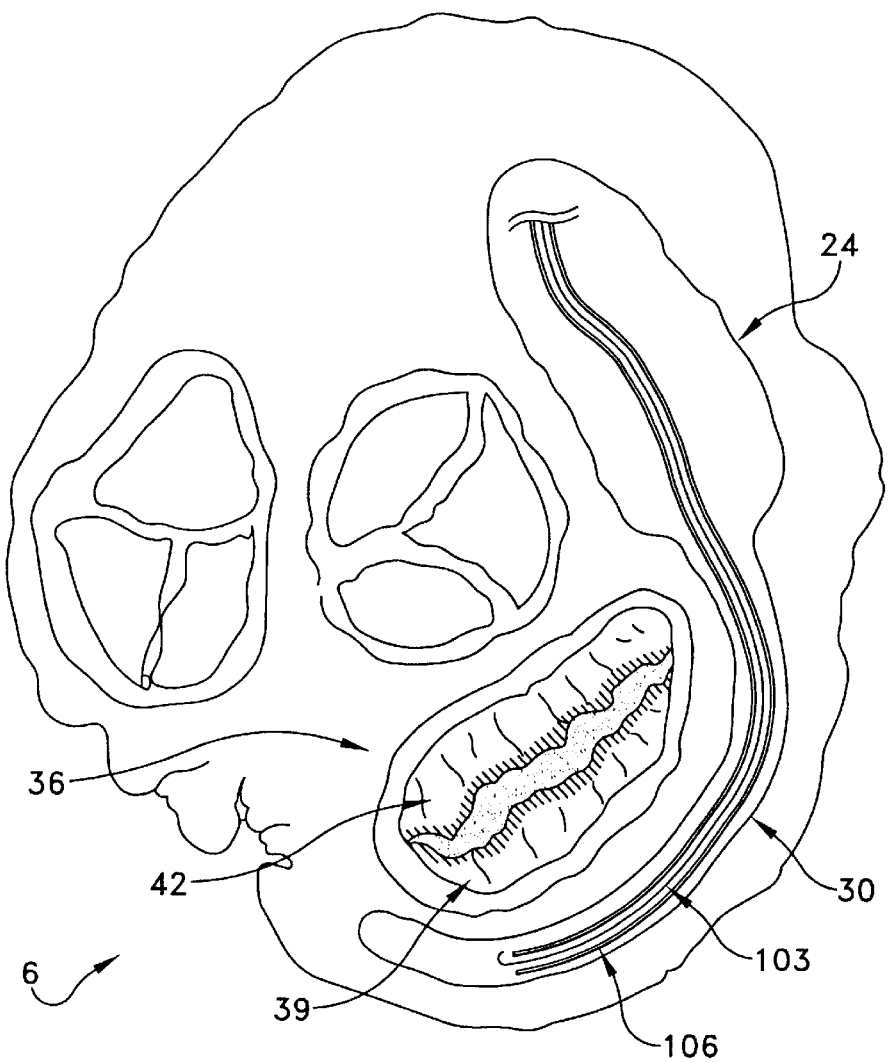

Next, distal end 127 of delivery catheter 106 is placed over proximal end 118 of guidewire 103 and passed down the guidewire until the distal end of the delivery catheter is positioned in coronary sinus 30. See FIG. 5. Again, it will be appreciated that as the flexible delivery catheter 106 passes down the coronary sinus, the delivery catheter will tend to assume the natural curved shape of the coronary sinus, due to the flexible nature of the delivery catheter.

Figure 6:
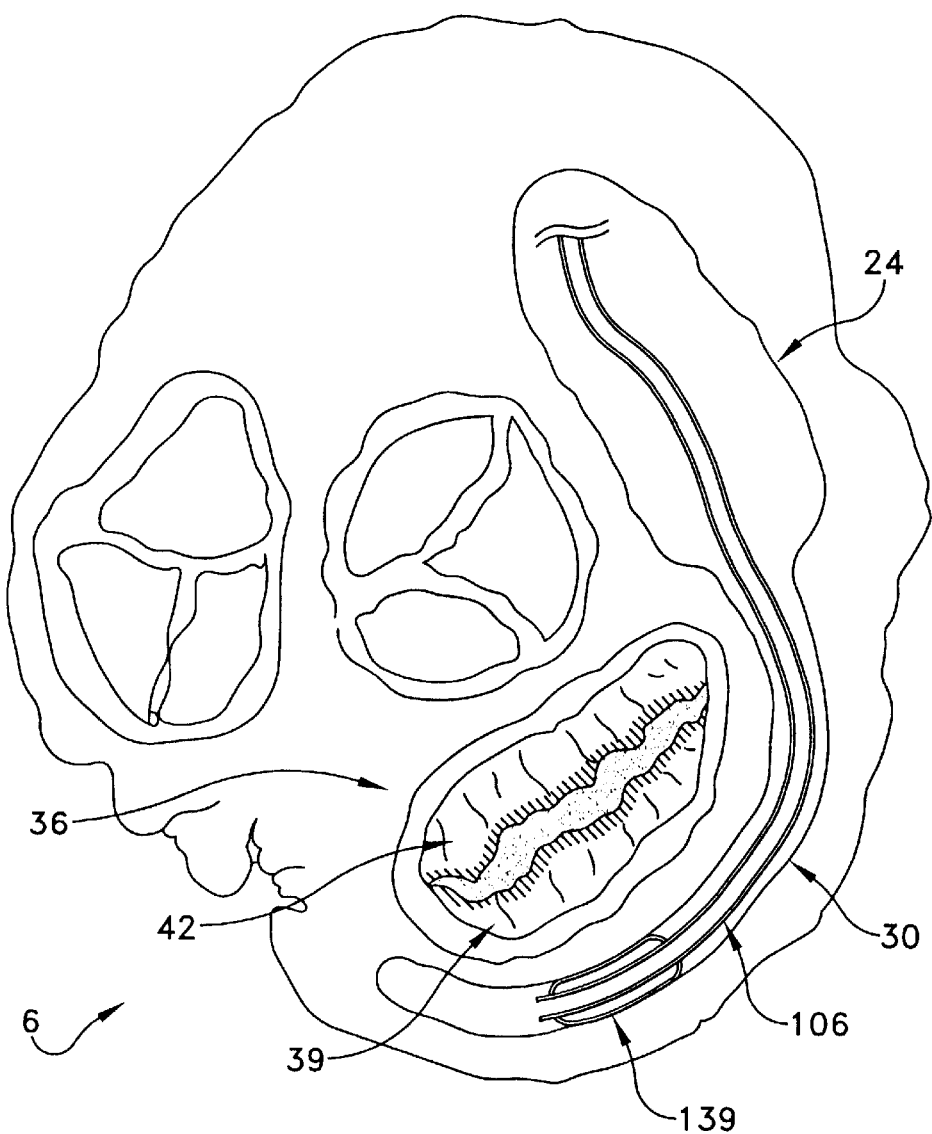

Once delivery catheter 106 has been positioned within the coronary sinus, guidewire 103 is removed. See FIG. 6. Either before or after guidewire 103 is removed, balloon 139 lay be inflated so as to secure distal end 127 of delivery catheter 106 in position within coronary sinus 30.

Next, push rod 109 is passed down the central lumen 136 of delivery catheter 106. As the push rod's straight, substantially rigid elongated body 157 is passed down central lumen 136 of delivery catheter 106, it will force the delivery catheter to assume a straight configuration at the point where the straight, substantially rigid elongated body 157 currently resides. As push rod 109 is pushed down delivery catheter 106, balloon 139 will hold the distal end of the delivery catheter in position within coronary sinus 30.

Push rod 109 is pushed down delivery catheter 106, utilizing removable proximal stiffener 160 as needed, until the straight, substantially rigid elongated body 157 is located adjacent to the posterior annulus of mitral valve 36. See FIG. 7. As this occurs, the presence of the straight, substantially rigid elongated body 157 in delivery catheter 106 will cause at least a portion of coronary sinus 30 to assume a substantially straight configuration at this point, so that the posterior annulus of mitral valve 36 is forced anteriorly. This will cause the mitral valve's posterior leaflet 39 to also move anteriorly so as to improve mitral valve leaflet coaptation and thereby reduce (or completely eliminate) mitral valve regurgitation. In this respect it should be appreciated that the posterior annulus may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like. Using standard visualization means (e.g. echocardiography or fluoroscopy), the exact position of the straight, substantially rigid elongated body 157 is adjusted so as to reduce (or completely eliminate) regurgitation in mitral valve 36.

In this respect it should be appreciated that the straight, substantially rigid elongated body 157 is preferably sized to be somewhat less than the length of the coronary sinus between coronary ostium 27 and AIV 32. However, in some circumstances it may be desirable to size the straight, substantially rigid elongated body 157 so that it will extend out of the coronary sinus and into the right atrium.

Furthermore, it should also be appreciated that the system provides a degree of tactile feedback to the user during deployment. More particularly, substantial resistance will typically be encountered as the straight, substantially rigid elongated body 157 is pushed out of right atrium 24 and into coronary sinus 30; then resistance will typically drop as body 157 is moved through the coronary sinus; and then resistance will typically increase significantly again as the distal tip of body 157 comes to the far end 31 of the coronary sinus. Thus, there is a sort of tactile "sweet spot" when the straight, substantially rigid elongated body 157 is located in the coronary sinus between coronary ostium 27 and AIV 32, and this tactile "sweet spot" can be helpful to the user in positioning the straight, substantially rigid elongated body 157 in coronary sinus 30.

At this point the straight, substantially rigid elongated body 157 is locked in position, e.g., by closing adjustable valve 133, and balloon 139 may be deflated.

System 100 is left in this position until it is no longer needed. In some cases this may mean that system 100 is left in position for a period of a few hours, days or weeks; in other cases system 100 may be substantially permanent. If and when system 100 is to be removed, push rod 109 is removed from delivery catheter 106, and then delivery catheter 106 is removed from the patient.

Thus it will be seen that with the present invention, the straight, substantially rigid elongated body 157 is essentially force-fit into the normally curved portion of the coronary sinus adjacent to the mitral valve's posterior leaflet. By properly sizing the length of the straight, substantially rigid elongated body 157 relative to the natural curvature of the patient's anatomy, and by properly positioning the straight, substantially rigid elongated body 157 in the patient's coronary sinus, the straight, substantially rigid elongated body will cause at least a portion of the coronary sinus to assume a substantially straight configuration adjacent to the posterior leaflet of the mitral valve. This action will in turn drive the posterior annulus of the mitral valve anteriorly, so as to improve leaflet coaptation and thereby reduce mitral regurgitation. Thus, by inserting the straight, substantially rigid elongated body 157 into the coronary sinus adjacent to the posterior leaflet of the mitral valve, the annulus of the mitral valve is effectively manipulated so that it will assume an increased radius of curvature.

It has also been found that by inserting the straight, substantially rigid elongated body into the coronary sinus adjacent to the posterior leaflet of the mitral valve, the left ventricle may also be remodeled so as to help alleviate congestive heart failure.

Figure 7:
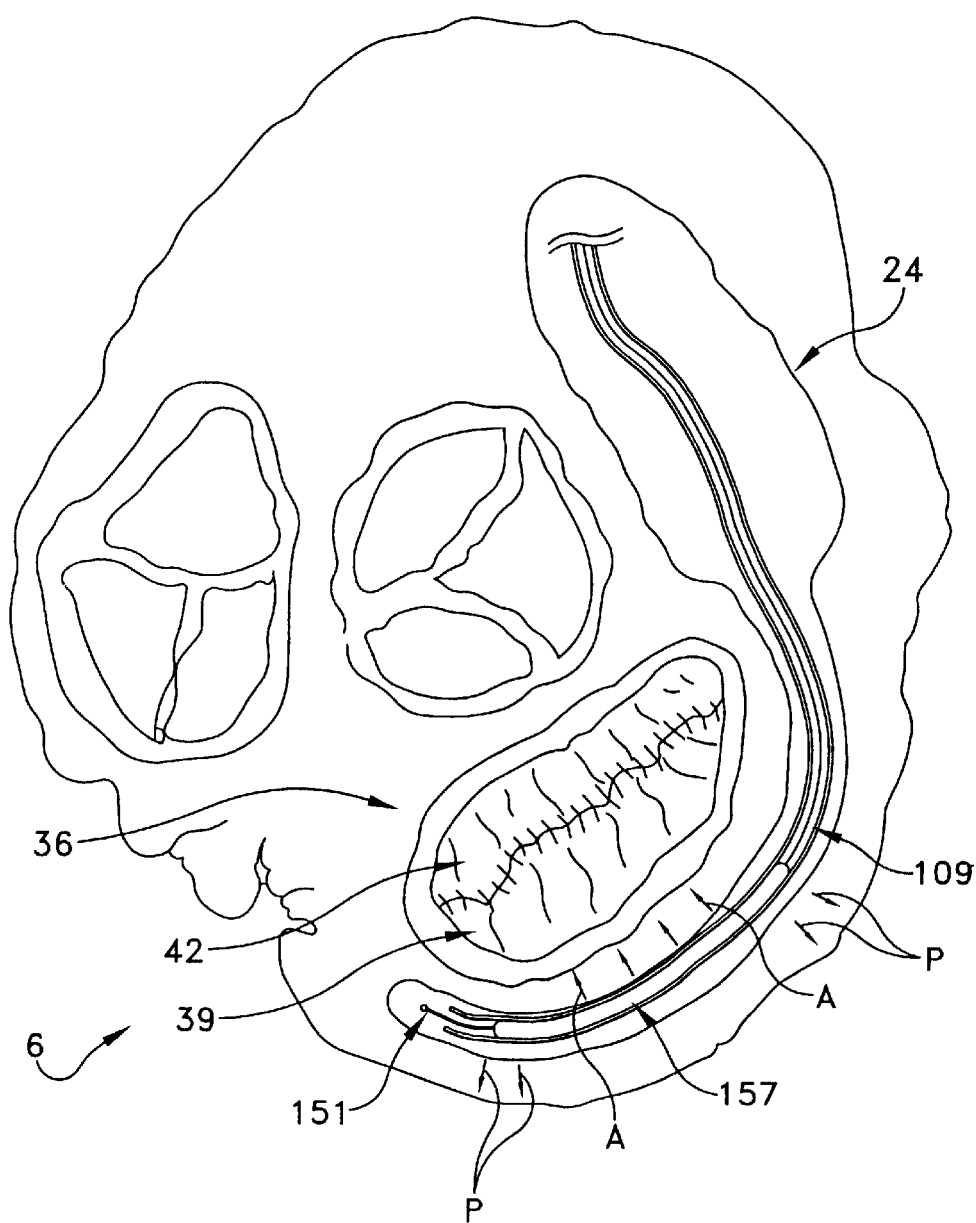

It is significant to note that with the present invention, the distal and proximal ends of straight, substantially rigid elongated body 157 apply a posteriorly-directed force on the walls of coronary sinus 30 (e.g., as shown with arrows P in FIG. 7) while the intermediate portion of straight, substantially rigid elongated body 157 applies an anteriorly-directed force on the walls of coronary sinus 30 (e.g., as shown with arrows A in FIG. 7).

Figure 8:
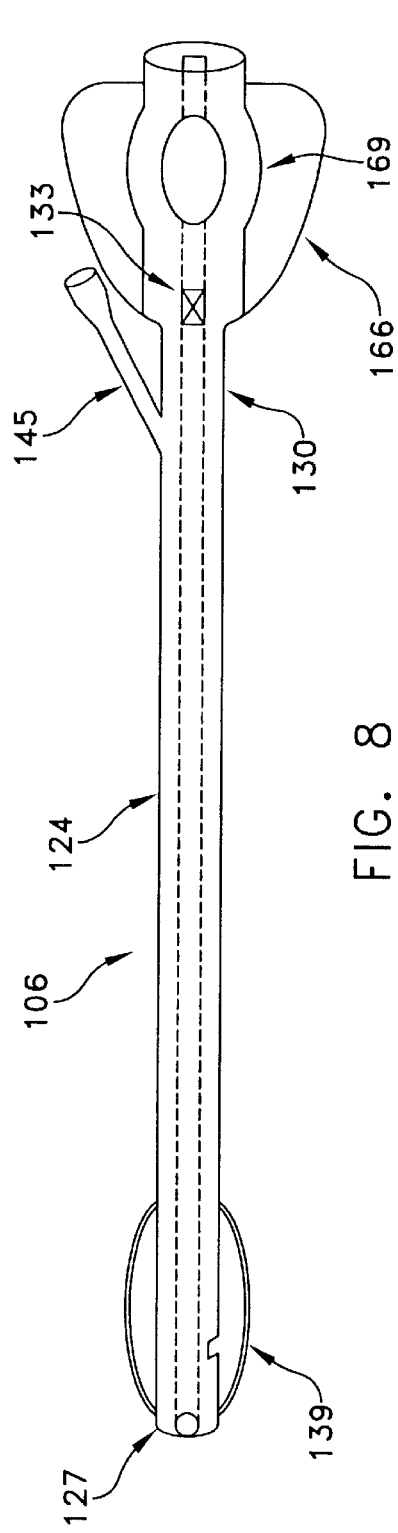
FIG. 8 shows an alternative form of delivery catheter.

In some cases the proximal end 130 of delivery catheter 106 may be fixed to the patient's outer skin using standard patient care methods such as adhesive tape, pursestring sutures, skin staples, etc. In other cases proximal end 130 of delivery catheter 106 may include a sewing cuff whereby the delivery catheter may be secured to the patient's tissue by suturing. See, for example, FIG. 8, where a sewing cuff 166 is shown attached to the proximal end 130 of delivery catheter 106. If desired, an element 169 may be provided proximal to adjustable valve 133, whereby flexible push rod 109 may be made fast to delivery catheter 106. By way of example, element 169 may comprise a crimpable element to secure flexible push rod 109 to delivery catheter 106, which is in turn secured to the patient. If desired, the proximal end of the assembly may be embedded under the skin of the patient, e.g., in the case of a permanent implant.

As noted above, it can be helpful to anchor the distal end of delivery catheter 106 in position within the coronary sinus prior to pushing push rod 109 into the delivery catheter. Such an arrangement will keep the delivery catheter in place as the push rod makes the turn within the right atrium and enters the coronary sinus. In the absence of such anchoring, the push rod may drive the delivery catheter down the inferior vena cava 21. By securing the distal end of delivery catheter 106 to the walls of coronary sinus 30, the delivery catheter can be stabilized against diversion down the inferior vena cava 21 when the straight, substantially rigid elongate body 157 encounters initial resistance to making the turn into the coronary sinus.

The balloon 139 is one way of accomplishing such anchoring. However, it is also possible to utilize other types of securing mechanisms to anchor the distal end 127 of delivery catheter 106 in position within coronary sinus 30, e.g., spring clips, ribs, etc.

Figure 9:
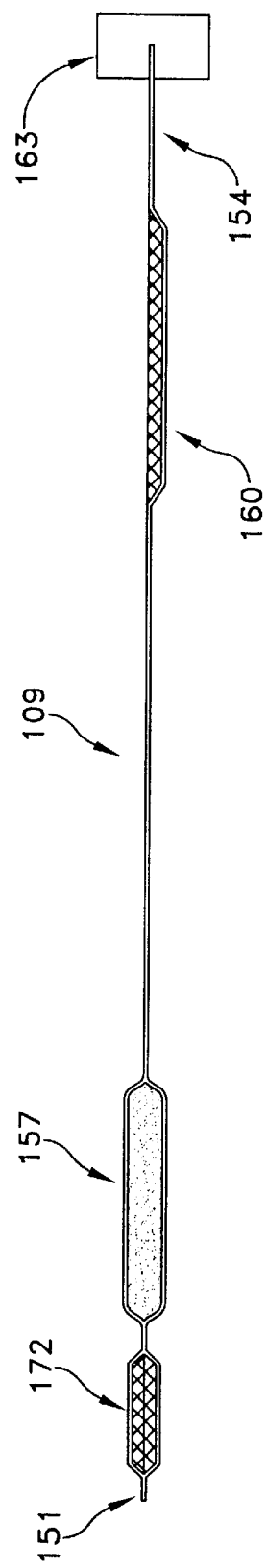
FIG. 9 shows an alternative form of flexible push rod.

Alternatively, and looking next at FIG. 9, the distal end 151 of push rod 109 may itself be provided with a distal anchor, e.g., such as the distal anchor 172 shown in FIG. 9.

Figure 9A:
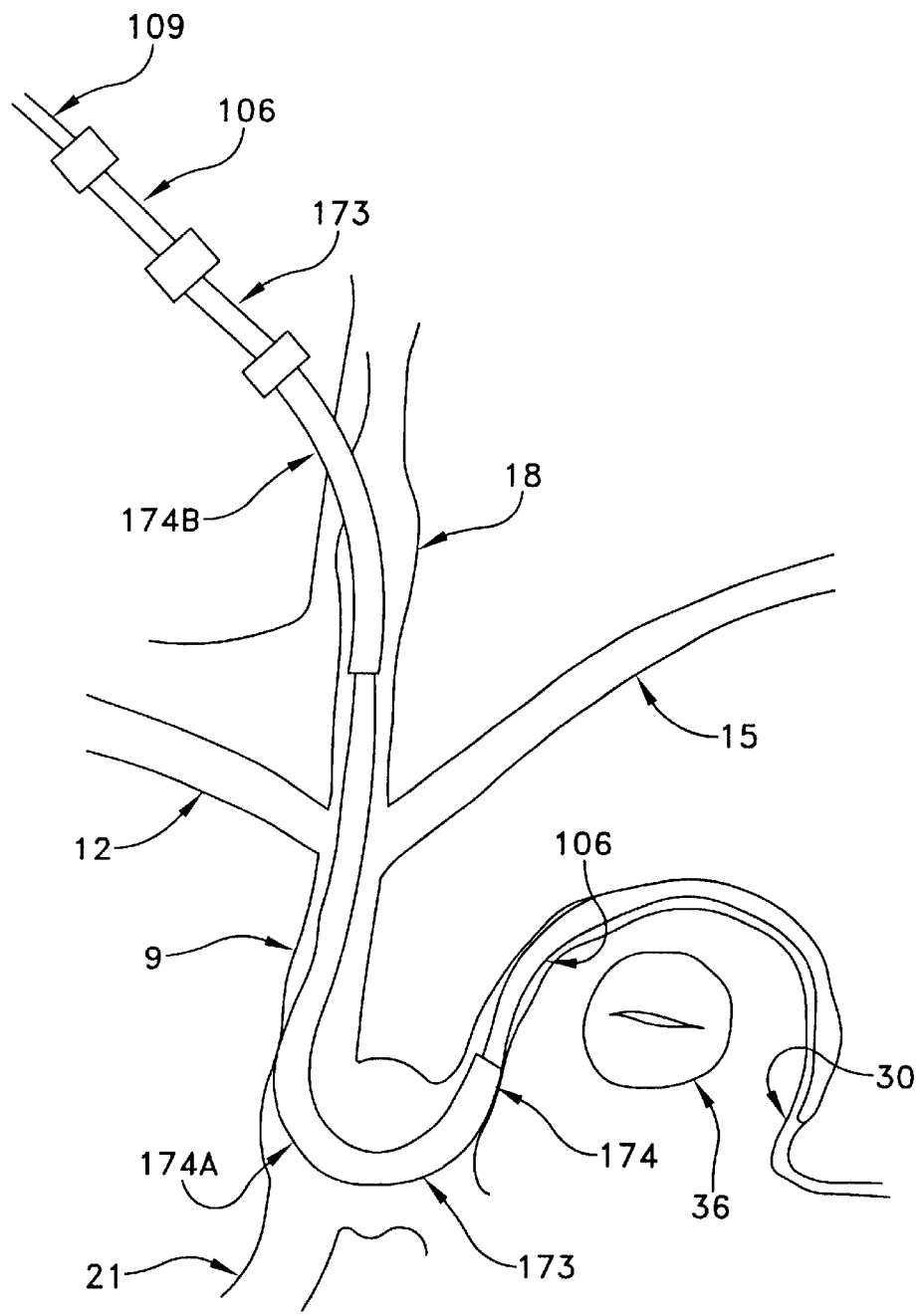
FIG. 9A shows another alternative form of the present invention.

It is also possible to prevent diversion of delivery catheter 106 down inferior vena cava 21 without anchoring the distal end of delivery catheter 106 or flexible push rod 109 to the walls of the coronary sinus. More particularly, and looking now at FIG. 9A, there is shown a support catheter 173 which is formed out of a more rigid material than delivery catheter 106. Support catheter 173 is constructed so that its distal end 174 can be positioned in coronary ostium 27 and then its sidewall 174A can support delivery catheter 106 adjacent to inferior vena cava 21 when push rod 109 is passed down delivery catheter 106, whereby to prevent delivery catheter 106 from diverting down inferior vena cava 106. FIG. 9A also shows an introducer catheter 174B at the entrance to jugular vein 18.

As noted above, as push rod 109 is advanced to the region adjacent to the posterior annulus of the mitral valve, the straight, substantially rigid elongated body 157 will distort the natural configuration of the coronary sinus so that it will assume a substantially straight configuration. While this action induces the desired valve remodeling, it can also induce a significant stress on the walls of the coronary sinus, particularly at the distal and proximal ends of the straight, substantially rigid elongated body 157, where stress will be concentrated. To this end, the construction of the straight, substantially rigid elongated body 157 may be modified somewhat so as to better distribute this stress. More particularly, and looking next at FIG. 10, the distal and proximal ends of straight, substantially rigid elongated body 157 may include relatively flexible portions 175 to help better distribute the stress exerted on the walls of the coronary sinus. Additionally, and/or alternatively, any taper applied to the distal and proximal ends of straight, substantially rigid elongated body 157 may be elongated, e.g., such as shown at 178 in FIG. 11, so as to better distribute the stress imposed on the walls of the coronary sinus.

Figure 12:
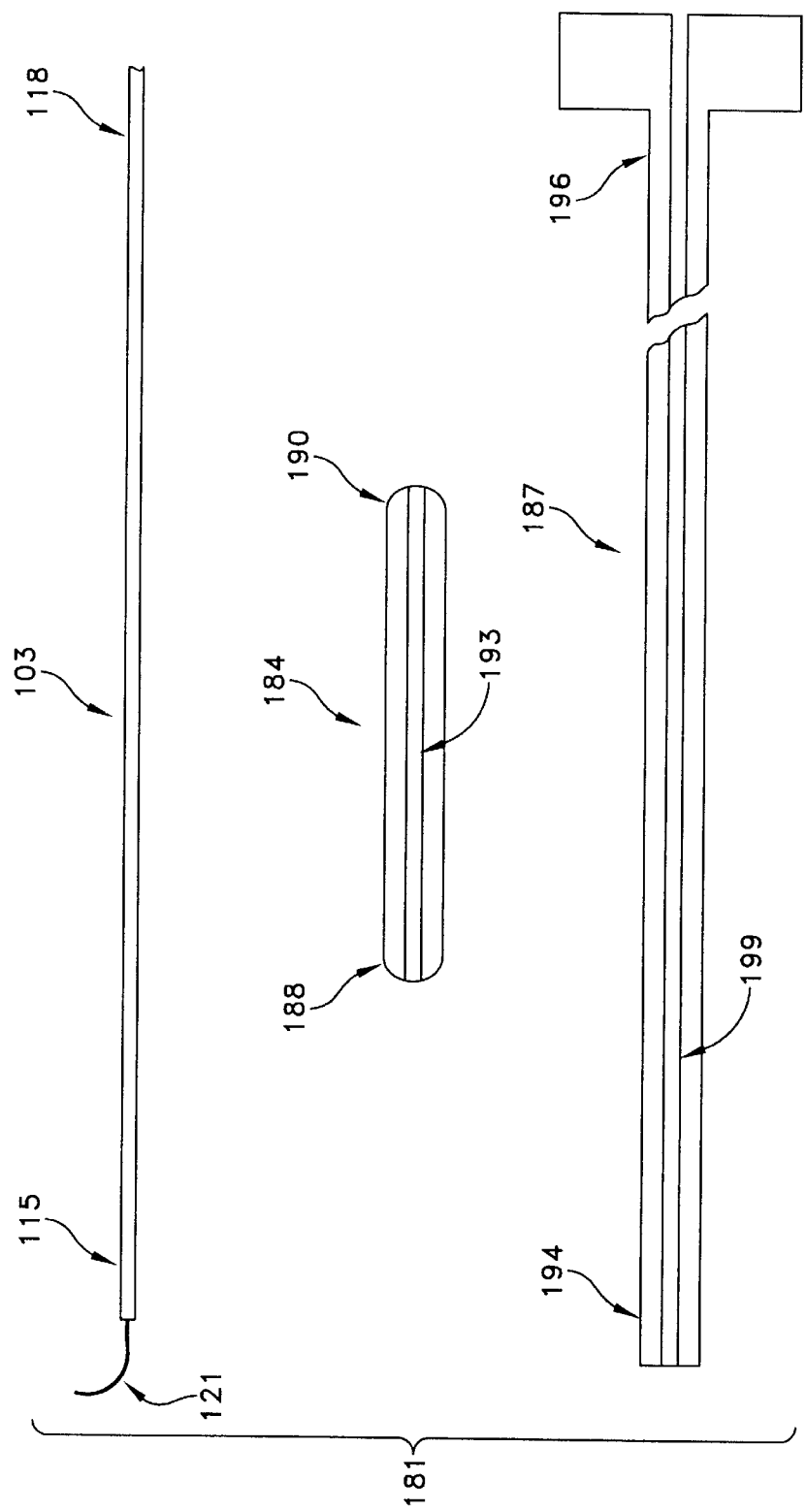
FIG. 12 shows an alternative system formed in accordance with the present invention.

Looking next at FIG. 12, there is shown a system 181 which comprises another preferred embodiment of the present invention. More particularly, system 181 generally comprises the guidewire 103, a straight, substantially rigid elongated body 184 and a push cannula 187.

Guidewire 103 is as previously described.

Straight, substantially rigid elongated body 184, which may have a variety of different lengths, comprises a distal end 188 and a proximal end 190. A central lumen 193 extends between distal end 188 and proximal end 190. Central lumen 193 accommodates guidewire 103.

Push cannula 187 comprises a distal end 194 and a proximal end 196. A central lumen 199 extends between distal end 194 and proximal end 196. Central lumen 199 accommodates guidewire 103.

System 181 may be used as follows to reduce mitral regurgitation.

First, distal end 115 of guidewire 103 is passed down jugular vein 18 (or the left subclavian vein 15) of a patient, down superior vena cava 9, through right atrium 24 of the heart, and into coronary sinus 30. It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 will help minimize damage to vascular structures as the guidewire is advanced into position.

Figure 13:
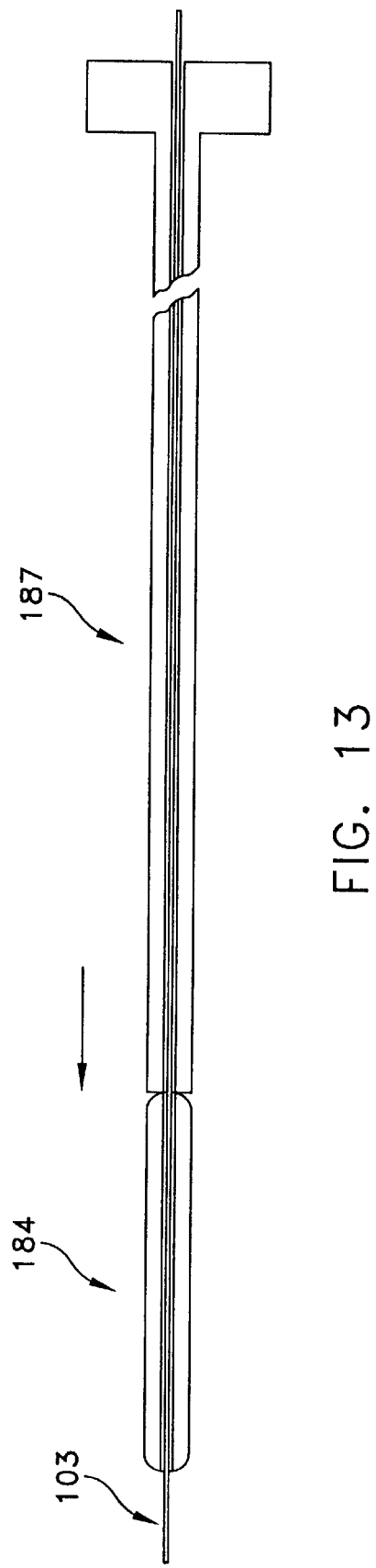
FIG. 13 shows use of the system shown in FIG. 12.

Next, distal end 188 of straight, substantially rigid elongated body 184 is placed over proximal end 118 of guidewire 103 and passed a short distance down the guidewire. Then the distal end 194 of push cannula 187 is placed over proximal end 118 of guidewire 103, and then push cannula 187 is advanced down the guidewire. As push cannula 187 is advanced down the guidewire, its distal end 194 pushes the straight, substantially rigid elongated body 184 ahead of it. See FIG. 13.

As the straight, substantially rigid elongated body 184 is passed down the coronary sinus, it will force the coronary sinus to assume a straight configuration at the point where the straight, substantially rigid elongated body 184 currently resides. Push cannula 187 is pushed down guidewire as needed, until the straight, substantially rigid elongated body 184 is located adjacent to the posterior annulus of the mitral valve. As this occurs, the presence of the straight, substantially rigid elongated body 184 in the coronary sinus will cause coronary sinus to assume a substantially straight configuration at this point, so that the posterior annulus of mitral valve is forced anteriorly. This will cause the posterior mitral valve leaflet to also move anteriorly so as to improve leaflet coaptation and thereby reduce (or completely eliminate) mitral valve regurgitation. Using standard visualization means (e.g. echocardiography or fluoroscopy), the exact position of the straight, substantially rigid elongated body may be adjusted so as to reduce (or completely eliminate) regurgitation in the mitral valve.

If desired, the push cannula 187 may be provided with a releasably attachable interface (e.g., a grasper) so that it may releasably secure the proximal end 190 of the straight, substantially rigid elongated body 184. Such a feature will permit the straight, substantially rigid elongated body to be pulled backward within the coronary sinus, either for positioning or removal purposes.

Alternatively, elongated body 184 or 157 may have any of a variety of non-straight shapes along its length. For example, the elongated body may be wavy, spiraled, or curved along all or a portion of its length. By way of example, elongated body 157 and/or 184 may have a curved configuration so as to invert the natural curvature of the coronary sinus, i.e., so that it is bowed towards the anterior annulus. Or the elongated body may have a compound shape along its length, e.g., it may have a sort of "w" shape, with the center of the "w" being directed towards the anterior annulus. Any of these or other alternate shapes may effect the anterior displacement of the posterior annulus that results in reduction of the mitral valve regurgitation.

In other alternative embodiments, the elongated body may be flexible along at least a portion of its length. Regional flexibility and regional stiffness may allow for straightening of select locations of the coronary sinus and corresponding locations of the posterior mitral annulus. This can cause regions of the mitral annulus to move anteriorly, thus causing regional improvements in leaflet coaptation. In addition, the elongated body may be formed by two end segments connected together by a filament: by anchoring the two end segments relative to the anatomy and pulling the filament taught, the naturally curved wall of the coronary sinus can be straightened, whereby to move the posterior mitral annulus anteriorly and thereby reduce mitral regurgitation.

It is to be understood that the present invention is by no means limited to the particular constructions herein disclosed and/or shown in the drawings, but also comprises any modifications or equivalents within the scope of the claims.

What is claimed is:

1. A method for reducing mitral regurgitation comprising:
inserting an elongated substantially straight apparatus into the coronary sinus of a patient in the vicinity of the posterior leaflet of the mitral valve, the apparatus having a distal end, a proximal end, and an intermediate portion, and being so configured that the distal and proximal ends apply a posteriorly-directed force to the posterior wall of the coronary sinus and the intermediate portion applies an anteriorly-directed force to the anterior wall of the coronary sinus, to straighten the natural curvature of at least a portion of the coronary sinus in the vicinity of the posterior leaflet of the mitral valve, whereby to move the posterior annulus anteriorly and thereby improve leaflet coaptation.

2. A method for reducing mitral regurgitation comprising:
inserting an elongated substantially straight apparatus into the coronary sinus of a patient in the vicinity of the posterior leaflet of the mitral valve, the apparatus having a distal end, a proximal end, and an intermediate portion, and being so configured that the distal and proximal ends apply a posteriorly-directed force to the posterior wall of the coronary sinus and the intermediate portion applies an anteriorly-directed force to the anterior wall of the coronary sinus, to move at least a portion of the coronary sinus in the vicinity of the posterior leaflet of the mitral valve anteriorly, whereby to move the posterior annulus anteriorly and thereby improve leaflet coaptation.

3. A method for reducing mitral regurgitation comprising:
inserting an elongated substantially straight apparatus into the coronary sinus of a patient in the vicinity of the posterior leaflet of the mitral valve, the apparatus having a distal end, a proximal end, and an intermediate portion, and being so configured that the distal and proximal ends apply a posteriorly-directed force to the posterior wall of the coronary sinus and the intermediate portion applies an anteriorly-directed force to the anterior wall of the coronary sinus, to reduce the degree of natural curvature of at least a portion of the coronary sinus in the vicinity of the posterior leaflet of the mitral valve, whereby to move the posterior annulus anteriorly and thereby improve leaflet coaptation.

4. A method for reducing mitral regurgitation comprising:
inserting an elongated substantially straight apparatus into the coronary sinus of a patient in the vicinity of the posterior leaflet of the mitral valve, the apparatus having a distal end, a proximal end, and an intermediate portion, and being so configured that the distal and proximal ends apply a posteriorly-directed force to the posterior wall of the coronary sinus and the intermediate portion app lies an anteriorly-directed force to the anterior wall of the coronary sinus, to increase the natural radius of curvature of at least a portion of the coronary sinus in the vicinity of the posterior leaflet of the mitral valve, whereby to move the posterior annulus anteriorly and thereby improve leaflet coaptation.

5. A method for reducing mitral regurgitation comprising:
inserting an elongated substantially straight apparatus into the coronary sinus of a patient in the vicinity of the posterior leaflet of the mitral valve, the apparatus having a distal end, a proximal end and an intermediate portion, the apparatus being configured so that when the apparatus is positioned in the coronary sinus in the vicinity of the posterior leaflet of the mitral valve, the distal and proximal ends apply a posteriorly-directed force to the posterior wall of the coronary sinus and the intermediate portion applies an anteriorly-directed force to the anterior wall of the coronary sinus, whereby to move the posterior annulus anteriorly and thereby improve leaflet coaptation.

6. A method according to the claim 5 wherein the apparatus is fixed on a push rod and the step of inserting the apparatus into the coronary sinus comprises advancing the push rod into the coronary sinus until the apparatus is positioned in the coronary sinus in the vicinity of the posterior leaflet of the mitral valve.

7. A method according to claim 6 wherein a delivery catheter is advanced into the coronary sinus until a distal portion thereof is in the vicinity of the posterior leaflet, and the push rod is subsequently advanced through the delivery catheter.

8. A method according to claim 7 wherein a guidewire is advanced into the coronary sinus until a distal portion thereof is in the vicinity of the posterior leaflet, thereafter the delivery catheter is advanced into the coronary sinus, the guidewire is withdrawn from the patient, and thereafter the push rod is advanced through the delivery catheter.

9. A method according to claim 7 wherein the apparatus is guided into position by the delivery catheter, and prior to advancing the delivery catheter a support catheter is pre-positioned such that the delivery catheter is advanced through the support catheter.

10. A method according to claim 6 wherein the push rod is advanced by manipulation of a handle fixed on the push rod proximate a proximal end of the push rod.

11. A method according to claim 5 wherein the step of inserting the apparatus into the coronary sinus comprises advancing a guidewire into the coronary sinus and to the vicinity of the posterior leaflet of the mitral valve, providing the apparatus having an axial central lumen extending therethrough, mounting the apparatus on the guidewire for sliding movement thereon, mounting a push cannula on the guidewire so as to slide along the guidewire, and pushing the push cannula to thereby push the apparatus into the vicinity of the posterior leaflet.

12. A method according to claim 11 and comprising the further steps of withdrawing the push cannula, and withdrawing the guidewire.

13. A method for reducing mitral regurgitation comprising:
    inserting a substantially straight elongated body having a distal end, a proximal end, and an intermediate portion into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, the body ends apply a posteriorly-directed force to the posterior wall of the coronary sinus and the body intermediate portion applies an anteriorly-directed force to the anterior wall of the coronary sinus, to cause at least a portion of the coronary sinus to assume a substantially straight configuration adjacent to the posterior leaflet of the mitral valve, whereby to increase the radius of curvature of the mitral annulus and thereby improve leaflet coaptation.

14. A method for reducing mitral regurgitation comprising:
    inserting a substantially rigid and substantially straight elongated body having a distal end, a proximal end, and an intermediate portion into the coronary sinus of a patient in the vicinity of the posterior leaflet of the mitral valve, the elongated body being configured relative to the natural curvature of the coronary sinus in the vicinity of the posterior leaflet of the mitral valve so that when the elongated body is positioned in the coronary sinus, the body ends apply a posteriorly-directed force to the posterior wall of the coronary sinus and the body intermediate portion applies an anteriorly-directed force to the anterior wall of the coronary sinus, to cause at least a portion of the coronary sinus to assume a different configuration adjacent to the posterior leaflet of the mitral valve, whereby to move the posterior annulus anteriorly and thereby improve leaflet coaptation.

15. A method for reducing mitral regurgitation comprising:
    inserting a substantially straight, substantially rigid elongated body having a distal end, a proximal end, and an intermediate portion into the coronary sinus of a patient in the vicinity of the posterior leaflet of the mitral valve, the length of the elongated body being sized relative to the natural curvature of the coronary sinus in the vicinity of the posterior leaflet of the mitral valve so that when the elongated body is positioned in the coronary sinus, the body ends apply a posteriorly-directed force to the posterior wall of the coronary sinus and the body intermediate portion applies an anteriorly-directed force to the anterior wall of the coronary sinus, to cause at least a portion of the coronary sinus to assume a substantially straight configuration adjacent to the posterior leaflet of the mitral valve, whereby to increase the radius of curvature of the mitral annulus and thereby improve leaflet coaptation.

16. A method according to claim 13 wherein the elongated body is inserted into the coronary sinus.

17. A method according to claim 16 wherein the elongated body is inserted into the coronary sinus by introducing the elongated body into the patient's jugular vein, passing the down the superior vena cava, passing the body through the right atrium and then passing 14 the body into the coronary sinus.

18. A method according to claim 16 wherein the elongated body is inserted into the coronary sinus by introducing the elongated body into the patient's left subclavian vein, passing the body down the superior vena cava, passing the body through the right atrium and then passing the body into the coronary sinus.

19. A method according to claim 15 wherein the elongated body is inserted into the coronary sinus through an incision in the patient's heart.

20. A method according to claim 15 wherein the elongated body is guided into position by passing the body through a pre-positioned delivery catheter.

21. A method according to claim 20 wherein the elongated body is guided into position by inserting a guidewire into the coronary sinus, passing the delivery catheter over the guidewire and into the coronary sinus, removing the guidewire, and then passing the elongated body down the delivery catheter.

22. A method according to claim 15 wherein the elongated body is guided into position by passing the body over a pre-positioned guidewire.

23. A method according to claim 22 wherein the elongated body is guided into position by inserting a guidewire into the coronary sinus and then passing the elongated body down the guidewire.

24. A method according to claim 15 further comprising the subsequent step of removing the elongated body from the coronary sinus.

25. A method according to claim 15 wherein the elongated body is inserted under visualization.

26. A method according to claim 15 wherein the visualization is achieved by using a procedure chosen from the group consisting of fluoroscopy, echocardiography, intravascular ultrasound, angioscopy and real-time magnetic resonance imaging.

27. A method according to claim 15 including the additional step of assessing the efficacy of the procedure.

28. A method according to claim 15 wherein said substantially straight, substantially rigid elongated body is guided into position without the use of a guide catheter and a guidewire.

29. Apparatus for reducing mitral regurgitation comprising:

an elongated substantially straight body having a distal end, a proximal end and an intermediate portion, the body being configured so that when the body is positioned in the coronary sinus in the vicinity of the posterior leaflet of the mitral valve, the distal and proximal ends apply a posteriorly-directed force to the posterior wall of the coronary sinus, and the intermediate portion applies an anteriorly-directed force to the anterior wall of the coronary sinus, whereby to move the posterior annulus of the mitral valve anteriorly and thereby improve leaflet coaptation.

30. Apparatus according to claim 29 wherein said body configuration is a selected one of (i) wavy, (ii) spiraled, (iii) curved in part, (iv) curved entirely, (v) curved inverted to the natural curvature of the coronary sinus, and (vi) "w" shaped.

31. Apparatus according to claim 29 wherein said body intermediate portion is substantially rigid and wherein said body ends are flexible.

32. Apparatus according to claim 29 wherein said body is provided with a central lumen extending therethrough, and said apparatus further comprises:

a guidewire dimensioned for slidable disposition in the body central lumen; and a cannula for sliding disposition on said guidewire;

whereby said body and said cannula are mountable on said guidewire and movement of said cannula on said guidewire in a distal direction pushes said body distally along said guidewire.

33. Apparatus for reducing mitral regurgitation comprising:

a substantially straight elongated body having a distal end, a proximal end and an intermediate portion, and adapted to be inserted into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, the body ends apply a posteriorly-directed force to the posterior wall of the coronary sinus and the body intermediate portion applies an anteriorly-directed force to the anterior wall of the coronary sinus, to cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

34. Apparatus for reducing mitral regurgitation comprising:

a substantially rigid and substantially straight elongated body having a distal end, a proximal end, and an intermediate portion, and adapted to be inserted into the coronary sinus of a patient in the vicinity of the posterior leaflet of the mitral valve, the length of the elongated body being sized relative to the natural curvature of the coronary sinus in the vicinity of the posterior leaflet of the mitral valve so that when the elongated body is positioned in the coronary sinus, the body applies a posteriorly-directed force to the posterior wall of the coronary sinus and applies an anteriorly-directed force to the anterior wall of the coronary sinus, to cause at least a portion of the coronary sinus to assume a different configuration adjacent to the posterior leaflet of the mitral valve, whereby to move the posterior annulus anteriorly and thereby improve leaflet coaptation.

35. Apparatus for reducing mitral regurgitation comprising:

a substantially straight, substantially rigid elongated body having a distal end, a proximal end, and an intermediate portion, and adapted to be inserted into the coronary sinus of a patient in the vicinity of the posterior leaflet of the mitral valve, the length of the elongated body being sized relative to the natural curvature of the coronary sinus in the vicinity of the posterior leaflet of the mitral valve so that when the elongated body is positioned in the coronary sinus, the body ends apply a posteriorly-directed force to the posterior wall of the coronary sinus and the body intermediate portion applies an anteriorly-directed force to the anterior wall of the coronary sinus, to cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

36. Apparatus according to claim 35 further comprising a delivery catheter adapted to be positioned within the coronary sinus of the patient, said delivery catheter being formed out of a flexible material so that it will substantially assume the configuration of the coronary sinus, said delivery catheter being adapted to receive said elongated body therein.

37. Apparatus according to claim 36 wherein said elongated body is mounted to a rod, wherein said rod is formed out of a flexible material so that said rod will assume the configuration of the coronary sinus, and further wherein said rod is sized to fit within said delivery catheter.

38. Apparatus according to claim 37 wherein said rod is provided with a handle portion proximate a proximal end of said rod, said handle portion facilitating manipulation of said rod to locate said body in the vicinity of the posterior leaflet.

39. Apparatus according to claim 36 further comprising a removable guidewire for positioning said delivery catheter in the coronary sinus.

40. Apparatus according to claim 39 wherein said guidewire is provided with a spring tip at a distal end thereof.

41. Apparatus according to claim 35 further comprising a guidewire adapted to be positioned within the coronary sinus, said guidewire being formed out of a flexible material so that it will substantially assume the configuration of the coronary sinus, and further wherein the elongated body is cannulated for riding along said guidewire.

42. Apparatus according to claim 35 wherein at least one of the distal and proximal ends of said elongated body includes a flexible portion for relieving stress imposed on the coronary sinus when said elongated body is disposed within the coronary sinus.

43. Apparatus according to claim 35 wherein at least one of the distal and proximal ends of said elongated body is tapered for relieving stress imposed on the coronary sinus when said elongated body is disposed within the coronary sinus.

44. Apparatus according to claim 35 wherein said elongated body has a length no longer than a segment of the coronary sinus located between the coronary ostium and the AIV.

45. Apparatus according to claim 36 wherein said apparatus further comprises a support catheter for preventing said delivery catheter from diverting into the inferior vena cava when said elongated body is passed through said delivery catheter.

46. A method for reducing mitral regurgitation comprising:

inserting an elongated substantially straight apparatus having a distal end, a proximal end and an intermediate portion into the coronary sinus of a patient in the vicinity of the posterior leaflet of the mitral valve, the apparatus being so configured that the apparatus ends apply a posteriorly-directed force to the posterior wall of the coronary sinus and the apparatus intermediate portion applies an anteriorly-directed force to the anterior wall of the coronary sinus, to invert the natural curvature of at least a portion of the coronary sinus in the vicinity of the posterior leaflet of the mitral valve, whereby to move the posterior annulus anteriorly and thereby improve leaflet coaptation.

47. Apparatus for reducing mitral regurgitation comprising:

an elongated substantially straight body having a distal end, a proximal end and an intermediate portion, and adapted to be inserted into the coronary sinus of a patient in the vicinity of the posterior leaflet of the mitral valve, the body being so configured that the body ends apply a posteriorly-directed force to the posterior wall of the coronary sinus and the body intermediate portion applies an anteriorly-directed force to the anterior wall of the coronary sinus, to invert the natural curvature of at least a portion of the coronary sinus in the vicinity of the posterior leaflet of the mitral valve, whereby to move the posterior annulus anteriorly and thereby improve leaflet coaptation.

* * * * *